(12) United States Patent
Peterson, Jr.

(10) Patent No.: US 12,151,040 B2
(45) Date of Patent: Nov. 26, 2024

(54) EXTENDING UV EMITTER LIFE

(71) Applicant: HEPCO HOLDINGS, LLC, St. Petersburg, FL (US)

(72) Inventor: Daniel J. Peterson, Jr., Lakeland, FL (US)

( * ) Notice: Subject to any disclaimer, the term of this patent is extended or adjusted under 35 U.S.C. 154(b) by 97 days.

(21) Appl. No.: 18/187,019

(22) Filed: Mar. 21, 2023

(65) Prior Publication Data

US 2024/0316230 A1 Sep. 26, 2024

(51) Int. Cl.
*A61L 2/10* (2006.01)
*A61L 2/24* (2006.01)
*A61L 2/26* (2006.01)

(52) U.S. Cl.
CPC .............. *A61L 2/10* (2013.01); *A61L 2/24* (2013.01); *A61L 2/26* (2013.01); *A61L 2202/11* (2013.01); *A61L 2202/14* (2013.01); *A61L 2202/26* (2013.01)

(58) Field of Classification Search
CPC ..... A61L 2/10; A61L 2/24; A61L 2/26; A61L 2202/11; A61L 2202/14; A61L 2202/26
See application file for complete search history.

(56) References Cited

U.S. PATENT DOCUMENTS

| | | | |
|---|---|---|---|
| 2,569,079 A | 10/1950 | Special | |
| 3,662,175 A | 5/1972 | Davidson | |
| 5,446,289 A | 8/1995 | Shodeen et al. | |
| 6,146,588 A | 11/2000 | Deighton | |
| 7,090,649 B2 | 8/2006 | Kang | |
| 7,344,272 B2 | 3/2008 | Cooper et al. | |
| 7,875,869 B1 | 1/2011 | Shadan | |
| 7,960,706 B2 | 6/2011 | Ullman | |
| 8,241,565 B1 | 8/2012 | Abdul | |
| 8,624,202 B2 | 1/2014 | Gil et al. | |
| 8,784,731 B2 | 7/2014 | Gil et al. | |
| 9,114,183 B2 | 8/2015 | Campagna | |
| 10,596,280 B1 | 3/2020 | Henderson | |
| 11,033,646 B1 | 6/2021 | McKeon | |

(Continued)

FOREIGN PATENT DOCUMENTS

| | | |
|---|---|---|
| EP | 2295112 A1 | 3/2021 |
| WO | WO2016179705 A1 | 11/2016 |
| WO | 2022139699 | 6/2022 |

OTHER PUBLICATIONS

Tianhong Dai et al., Ultraviolet C irradiation: an alternative antimicrobial approach to localized infections? Feb. 10, 2012.

(Continued)

*Primary Examiner* — Sean M Luck
(74) *Attorney, Agent, or Firm* — Larson & Larson; Frank Liebenow; Justin P. Miller

(57) ABSTRACT

A method and apparatus detect the presence of the feet of a user and emits ultraviolet light (and generate ozone) towards the feet of the user when the presence of the feet (e.g., feet or shoes) are detected. To increase the life of ultraviolet emitters within the device, the ultraviolet emitters are continuously powered (when a power source is connected). The method and apparatus include louvers or shutters that move by way of an electromechanical device from a closed position to an open position upon detecting force from the weight of the user and move from the open position to the closed position upon detecting when the weight of the user abates.

20 Claims, 5 Drawing Sheets

(56) References Cited

U.S. PATENT DOCUMENTS

| | | |
|---|---|---|
| 11,185,602 B1 * | 11/2021 | Leal-Quiroz ............ A61L 2/24 |
| 2001/0042842 A1 | 11/2001 | Leighley |
| 2003/0030015 A1 | 2/2003 | Waluszko |
| 2003/0088297 A1 | 5/2003 | Stoppler |
| 2003/0153962 A1 | 8/2003 | Cumbie |
| 2003/0163068 A1 | 8/2003 | Kang |
| 2004/0052702 A1 | 3/2004 | Shuman |
| 2004/0116984 A1 | 6/2004 | Spooner |
| 2004/0256581 A1 | 12/2004 | Au |
| 2004/0262241 A1 | 12/2004 | Socha |
| 2005/0013729 A1 | 1/2005 | Brown-Skrobot |
| 2005/0263015 A1 | 12/2005 | Mulgrew |
| 2006/0047329 A1 | 3/2006 | Krespi |
| 2006/0089687 A1 | 4/2006 | Spooner |
| 2006/0206173 A1 | 9/2006 | Gertner |
| 2007/0075268 A1 | 4/2007 | Harris |
| 2007/0092832 A1 | 4/2007 | Grossman |
| 2007/0164232 A1 | 7/2007 | Rolleri et al. |
| 2007/0185553 A1 | 8/2007 | Kennedy |
| 2007/0192986 A1 | 8/2007 | Garcia et al. |
| 2007/0208395 A1 | 9/2007 | Leclerc et al. |
| 2007/0274879 A1 | 11/2007 | Millikin |
| 2008/0103560 A1 | 5/2008 | Powell |
| 2008/0172113 A1 | 7/2008 | Gourgouliatos |
| 2008/0208297 A1 | 8/2008 | Gertner |
| 2008/0234786 A1 | 9/2008 | Cumbie |
| 2008/0294227 A1 | 11/2008 | Perez |
| 2008/0308748 A1 | 12/2008 | Burrows |
| 2008/0310996 A1 | 12/2008 | Kim |
| 2009/0065716 A1 | 3/2009 | Ullman |
| 2009/0143842 A1 | 6/2009 | Cumbie |
| 2009/0169426 A9 | 7/2009 | Toepfer et al. |
| 2009/0240310 A1 | 9/2009 | Kennedy |
| 2010/0049177 A1 | 2/2010 | Boone, III |
| 2010/0076526 A1 | 3/2010 | Krespi |
| 2010/0104470 A1 | 4/2010 | McCabe |
| 2010/0179469 A1 | 7/2010 | Hammond |
| 2011/0037002 A1 | 2/2011 | Johnson |
| 2011/0240883 A1 | 10/2011 | Ullman |
| 2012/0045363 A1 | 2/2012 | Gil |
| 2012/0310141 A1 | 12/2012 | Kornfield |
| 2012/0328474 A1 | 12/2012 | Campagna |
| 2013/0101461 A1 | 4/2013 | Gil et al. |
| 2013/0336839 A1 | 12/2013 | Gil |
| 2014/0170019 A1 | 6/2014 | Gil |
| 2014/0222117 A1 | 8/2014 | Bourke, Jr. |
| 2014/0264076 A1 | 9/2014 | Bettles |
| 2014/0277299 A1 | 9/2014 | Intintoli |
| 2014/0305470 A1 | 10/2014 | Desu-Kalyanam |
| 2015/0037201 A1 | 2/2015 | Armour |
| 2015/0238774 A1 | 8/2015 | Anderson |
| 2015/0290346 A1 | 10/2015 | Kassel |
| 2015/0359668 A1 | 12/2015 | Kornfield |
| 2016/0101202 A1 | 4/2016 | Gil |
| 2016/0114067 A1 | 4/2016 | Dobrinsky |
| 2016/0129279 A1 | 5/2016 | Ferolito |
| 2016/0158575 A1 | 6/2016 | Levatter |
| 2016/0175550 A1 | 6/2016 | Taylor |
| 2016/0287896 A1 | 10/2016 | Anderson |
| 2017/0035918 A1 | 2/2017 | Kassel et al. |
| 2018/0055960 A1 | 3/2018 | Reiber |
| 2018/0153367 A1 * | 6/2018 | Dombrowsky ...... H05B 47/115 |
| 2018/0322753 A1 | 11/2018 | Stibich |
| 2019/0060495 A1 | 2/2019 | Gil |
| 2019/0262487 A1 | 8/2019 | Gil |
| 2019/0321503 A1 * | 10/2019 | Warnell ................ A47L 23/266 |
| 2021/0316024 A1 | 10/2021 | Green |
| 2021/0330827 A1 | 10/2021 | Lucio |
| 2022/0047738 A1 | 2/2022 | Shah |
| 2022/0079414 A1 * | 3/2022 | Desu-Kalyanam ..... A47L 23/02 |
| 2022/0226519 A1 | 7/2022 | Kudo |
| 2022/0313850 A1 | 10/2022 | Baarman |
| 2023/0020383 A1 * | 1/2023 | Ford .......................... A61L 2/26 |

OTHER PUBLICATIONS

Boker, A., G. Rolz-Cruz, B. Cumbie, and A. Kimball. 2007. A single-center, prospective, open-label, pilot study of the safety, local tolerability, and efficacy of ultraviolet-C (UVC) phototherapy for the . . . Centers for Disease Control and Prevention.

Jesse Miller, Efficacy of an Ozone-Generating Whole-Shoe Disinfection Device at Three Time Points, NSF International—Applied Research Center, 789 N. Dixboro Rd. Ann Arbor, MI 48015, USA, Aug. 27, 2019.

* cited by examiner

EXTENDING UV EMITTER LIFE

BACKGROUND OF THE INVENTION

It is known that the rising problem of antibiotic resistance has led to fears that medicine will return to the situation of a century ago when extensive wounds and surgery often led to death due to uncontrollable infection. These fears have in turn spurred a major research effort to find alternative antimicrobial approaches which, it is hypothesized, will kill resistant micro-organisms while being unlikely to cause additional resistance to develop. At the present time many international research efforts to discovery new antimicrobials are underway. Recently, the emphasis is on how to take precautions against creating, and if possible eliminate multidrug resistance in concert with exploring new methods to kill pathogenic microorganisms. Karen et al. in "Tackling antibiotic resistance," Bush K, *Nat Rev Microbiol.* 2011 Nov. 2; 9 (12): 894-6, pointed out that the investigation of novel non-antibiotic approaches, which can prevent and protect against infectious diseases should be encouraged, and should be looked upon as a high-priority for research and development projects.

One source of sterilization is UV-C radiation (wavelength: 200-280 nm). Among this wavelength range, the optimum range of 250-270 nm has the best potential ability to inactivate microorganisms because it this wavelength is absorbed by nucleic acids of microbial cells and, therefore, is the most lethal range of wavelengths.

One way to reduce infection by resistant (or non-resistant) microorganisms is to neutralize as many of such organisms from the environment as possible. As some such organisms spread through the air, HEPA filters are often used to filter out such organisms before they infect humans, but many such organisms are transmitted on surfaces such as hands and shoes of people entering the area. To this, often before entering these areas, staff/patients must kill organisms from their hands using a germicidal compound or washing their hands. This helps keep microorganisms from spreading by way of hands, but what about the microorganisms that are carried on one's foot (e.g., shoe)?

Feet and footwear (shoes, sandals, socks, etc.) are carriers of multiple contamination agents that are often introduced into interiors of homes, hospital rooms, schools, and offices from various sources of contamination. Although any portion of the feet/footwear is known to carry/spread contamination, due to contact with contamination from surfaces (e.g., floor), the majority of contamination is carried on the bottom of footwear (or soles of feet).

Most contamination is inert, for example, dirt, sand, dust, leaves, etc. More serious contamination from pathogens carried by foot often lead to the spread of various diseases. A study by Dr. Charles Gerba, microbiologist and professor at the University of Arizona and The Rockport Company, made in 2008, confirmed this finding. The study measured germs and microbes collected on footwear. What was found was a large number of bacteria both on the bottom and inside of shoes; averaging 420,000 units of bacteria on the outside of the shoe, and almost 3000 on the inside. The tested footwear picked up 420,000 units of bacteria in just two weeks. The bacteria included *Escherichia coli*, known to cause intestinal and urinary tract infections, meningitis and diarrheal disease; *Klebsiella pneumonia*, a common source for wound and bloodstream infections as well as pneumonia; and *Serratia ficaria*, a rare cause of infections in the respiratory tract and wounds.

Such germs/microbes/pathogens, in addition to other chemicals, are picked up by the feet/shoes in one place and deposited in another, leading to the spread of contamination, possibly to the shoes of other people, etc.

Cleaning/vacuuming of the floor may help reduce exposure to such germs/microbes, but has little or no effect on many. Furthermore, the germs/microbes are not neutralized by vacuuming and pose a health risk when emptying the vacuum cleaner. Using steam cleaners to kill the bacteria was found ineffective in killing germs and bacteria in homes and public places. At the source, the steam has a temperature of at least 100 degrees C. but by the time the steam contacts the carpets or the floor, the temperature drops drastically and, therefore, the lower-temperature steam does not kill many bacteria and the viruses.

Applying chemical products by spraying or spreading on floors or carpets is also partially effective. To kill or disable most pathogens, a very strong chemical is required. As the strength of the chemical increases, so does the risk of potential hazards to health and safety of both the people applying the chemical and to the users of the cleaned surfaces. This is not to mention issues related to allergies. Stronger chemicals also tend to impact/discolor the surfaces on which they are applied. For example, bleach (chorine) is a known effective disinfectant, but bleach applied to one's shoes results in discolored shoes, and, therefore, would not be used by most people. Furthermore, bleach (chlorine) does not kill many pathogens that have a protective shell (e.g., MRSA).

The feet/shoes cause a major concern, especially in hospital settings. Often, hospitals have isolation wards for people that have highly contagious diseases such as necrotizing fasciitis and Methicillin-resistant *Staphylococcus aureus* (MRSA). The hospitals attempt to control the spread of such diseases by maintaining a negative air pressure in these wards (so air flows in when a door is opened), constant filtration of the air in the wards, constant germicidal treatment, wearing of disposable outer garments, etc. For the lower extremities, at most, workers use booties to cover their footwear. The use of booties is a weak attempt to solve the above noted problem of transmitting microorganisms by footwear, especially because the users of such booties use their hands to remove the cover from their feet.

The lack of diligence in reducing migration of microbes carried on feet/footwear is possibly responsible for an estimated 10% of new cases of disease such as MRSA each year, especially cases of such diseases that are contracted in hospitals. Many times, the hospitals are responsible for fighting these diseases without compensation due to the rationale that they were the source of the disease, resulting in billions of dollars in lost profits.

Beyond hospitals, many areas are also prone to breed germs/microbes and often travel on feet and shoes to homes, offices, etc. For example, public showers in gyms, schools, etc., often breed such microbes and, even after putting on shoes, these microbes get carried on the feet and shoes and often are deposited in homes and offices miles from the source.

Several techniques are known for reducing contamination from feet/shoes, especially for clean room environments in which it is important to limit particle contamination. For example, products used at the entrance to clean rooms include shoe vacuums with Hepa filters, sticky mats, and pressurized air flow to dislodge contaminates, all are only partially effective in removing/containing pathogens, while none actually kill germs.

UV radiation emitting devices (ultraviolet emitters or ultraviolet light bulbs) emit light with wavelengths of between, for example, 400-100 nm. Such ultraviolet light is known to kill at least a subset of known pathogens and, therefore, this light is suitable to reduce the number of pathogens on one's foot/shoe.

Although ultraviolet light kills some pathogens and is suitable for that purpose, ultraviolet radiation alone is not effective in killing certain pathogens or classes of pathogens, especially pathogens that have protective envelopes or shells that protect the pathogens from the environment until the pathogens find their way into a suitable environment for growth, such as a wound. An example of such a pathogen is C-diff, which has a hard outer shell and is not significantly affected by UVC radiation. Bleach has been found effective in breaking this outer shell and killing C-diff, but bleach is impractical for use on feet or shoes (see above).

Lower wavelengths of ultraviolet light will ionize oxygen producing ozone ($O_3$). For many uses of ultraviolet light, ozone ($O_3$) production is an unwanted side effect of ultraviolet lamps. For such uses, many ultraviolet lamps are treated/coated with a material that absorbs ultraviolet light wavelengths below 254 nm since these lower wavelengths of ultraviolet light will ionize oxygen and for many applications, the production of ozone is unwanted.

Ozone has been found to be effective in killing some pathogens that cannot be effectively killed with ultraviolet light alone. Ozone is a strong oxidizing agent that breaks through the encapsulation of some of the more difficult pathogens to kill such as C-diff. Ozone is effective in bacterial disinfection and the inactivation of many viruses. Therefore, it is preferred to use radiation emitting devices that emit ultraviolet light in approximately the 240-250 nm range (e.g., emitters without the above noted coating) while also emitting shorter wavelength ultraviolet light (e.g., approximately 180 nm) for the production of ozone in the presence of oxygen ($O_2$).

Such specialized lamps that do not have the surface treatment that filter out the 180 nm wavelengths are known and in use in other applications such as water sanitation, often known as germicidal lamps. These lamps are usually mercury vapor tubes similar to typical fluorescent light bulbs but without any phosphor coating and without any material that impedes the passing of ultraviolet light, including ultraviolet light in the 253.7 wavelength range which is very good at destroying pathogens. These radiation emitting devices emit a broader range of ultraviolet that includes the 254 nm wavelength and also shorter wavelengths (e.g., less than 240 nm) that break the bond between dioxygen molecules ($O_2+UV \rightarrow 2O$), then the unstable oxygen atoms bond with another dioxygen molecule ($O_2+O \rightarrow O_3$) forming ozone.

Unfortunately, these bulbs/emitters are costly and have limited bulb life. As the intended use for sanitizing the sole of a user's shoes, these bulbs are often mounted in enclosures that are affixed to the floor. As such, it is difficult and costly to replace these bulbs when they fail, especially when they fail prematurely. Further, it is often difficult to determine when a failure occurs as the bulbs/emitters are often only energized when the user's foot/shoe rest upon the device and, the foot/shoe will cover the emitters.

These bulbs/emitters often have an expected life based upon the manufacturer's testing. One reason for these bults/emitters premature failure is from power on/off cycles, just like many other types of emitters (e.g., fluorescent light bulbs). More stress is exerted on a bulb/emitter when it is powered on than when the bulb/emitter remains operation. For example, most incandescent or fluorescent bulbs fail when they are turned on as the heater/filament heat and expand/contract. In the example of mercury vapor lamps, premature failure is often due to fast temperature changes that occur when the mercury is vaporized. Although emissions of small amounts of ultraviolet light are minimal risks to health, it is not desirable to constantly emit significant amounts of ultraviolet light from a floor-mounted device as there are health risks from such emissions. Therefore, it is not desirable to constantly emit high concentrations of ultraviolet radiation from these floor-mounted foot sanitization devices. In the past, a sensor was deployed to signal when a foot/shoe was placed atop these floor-mounted devices and, power was provided to the ultraviolet bulbs in response to that signal. Unfortunately, this causes many on/off cycles, decreasing the life of the ultraviolet bulbs. Further, the typical ultraviolet emitting device have a non-zero turn-on time, often more than one second. It is desired that as soon as a user stands on the foot/shoe sanitizing device, ultraviolet light is emitted, and ozone is created.

What is needed is a foot/shoe sanitizing system that will provide fast-response UV light while extending the life of these bulbs/emitters.

SUMMARY OF THE INVENTION

Mechanisms are disclosed to detect the presence of the feet of a user and to emit the ultraviolet light (and generate ozone) when the presence of the feet (e.g., feet or shoes) are detected, without fully powering on, then powering off the ultraviolet bulbs. The mechanisms include one or more of louvers or shutters and/or reducing power to the ultraviolet bulbs, but not disconnecting power to the ultraviolet bulbs and, therefore, maintaining the highest possible ultraviolet bulb life. In some embodiments, the louver/shutter mechanism is completely mechanical such that the louvers/shutters open upon the weight of the user and close when the weight of the user abates. In some embodiments, a sensor detects the presence of the user's feet/shoes and signals an electro-mechanical mechanism to open the louvers/shutters until the user moves away.

In one embodiment, a foot/shoe sanitization device is disclosed including at least one ultraviolet emitter that is continuously powered to emit the ultraviolet light and is housed within an enclosure. A top section of the enclosure has at least one opening for passing ultraviolet light from the at least one ultraviolet emitter and towards the feet/shoe of a user. There is a mechanism for selectively occluding each of the at least one opening that has a first position in which each of the at least one opening allows passage of the ultraviolet light and a second position in which each of the at least one opening is occluded for blocking the passage of the ultraviolet light. The mechanism for selectively occluding is biased into the second position. There is a mechanism for detecting force applied to the top section of the enclosure. The mechanism for detecting force controls the mechanism for selectively occluding to move from the second position into the first position upon detecting a predetermined force applied to the top section, thereby, releasing the ultraviolet light through the at least one opening of the top section when the predetermined force is applied to the top section.

In another embodiment, a foot/shoe sanitization device is disclosed including at least one ultraviolet emitter housed within an enclosure that has a top section and a bottom section. A top section of the enclosure has at least one opening for passing ultraviolet light from the at least one ultraviolet emitter towards feet/shoes of a user. The at least one ultraviolet emitter is continuously powered to emit the ultraviolet light. A louver is slideably interfaced to the enclosure beneath the top section and has at least one louver opening. The louver is movable between a first position in which the at least one louver opening aligns with the at least one opening of the top section and a second position in which the louver blocks each of the at least one opening of the top section, the louver biased into the second position. Springs bias the top section of the enclosure away from the bottom section of the enclosure. A mechanical linkage is coupled between the top section of the enclosure and the bottom section of the enclosure such that, upon a predetermined force applied to the top section of the enclosure, the top section of the enclosure moves towards the bottom surface of the enclosure and the mechanical linkage moves the louver from the second position towards the first position, enabling the ultraviolet light to exit through the at least one opening of the top section.

In another embodiment, an method of sanitizing a foot/shoe is disclosed including upon receiving input power, continuously emitting ultraviolet light from at least one ultraviolet emitter housed within an enclosure and selectively occluding openings in a top section of the enclosure, thereby controlling an amount of the ultraviolet light escaping through the openings. Upon detecting a force applied to the top section of the enclosure, unblocking the openings in the top section, thereby increasing an amount of ultraviolet light leaving the enclosure through the openings and upon detecting abatement of the force applied to the top section of the enclosure, occluding the openings in the top section, thereby reducing the amount of ultraviolet light leaving the enclosure through the openings.

BRIEF DESCRIPTION OF DRAWINGS

The invention can be best understood by those having ordinary skill in the art by reference to the following detailed description when considered in conjunction with the accompanying drawings in which.

DETAILED DESCRIPTION OF THE INVENTION

Figure 1:
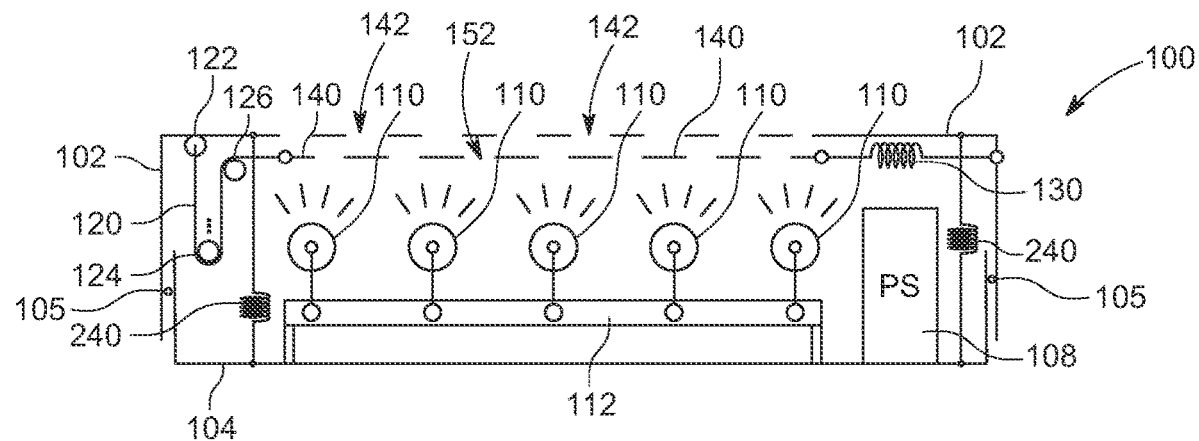
FIG. 1 illustrates a side-cutaway view of a foot sanitization device with louvers/shutters before downward pressure (weight) is placed on a top section.

Reference will now be made in detail to the presently preferred embodiments of the invention, examples of which are illustrated in the accompanying drawings. Throughout the following detailed description, the same reference numerals refer to the same elements in all figures.

Throughout the remainder of this description, the term "pathogen" will be used generically to denote any germ, virus, prion, fungus, spore, microbe, or other pathogen, capable or not capable of infecting a mammal such as a human.

The term louvers/shutters represents any such device or similar device that has at least two modes (e.g., positions), one in which light passes through the louvers/shutters and one in which light is blocked by the louvers/shutters.

Additionally, the described system is shown in detail for deployment concerning one specific mammal, a human being, though it is anticipated that such system in possibly other embodiments be used for other mammals such as dogs, cats, horses, cows, etc. Furthermore, the described system is disclosed in reference to feet and/or shoes for brevity and clarity purposes as it is fully understood that the described system will work for many objects including socks, slippers, etc. There are known risks of exposing certain parts of a mammal's body to certain wavelengths of ultraviolet light, therefore, it is anticipated that proper precautions are taken to reduce exposure to such and, therefore, reduce such risks.

For brevity, various mechanical subcomponents, supports, rubber feet, wires, etc., are not described as such are well known in the art.

Figure 2:
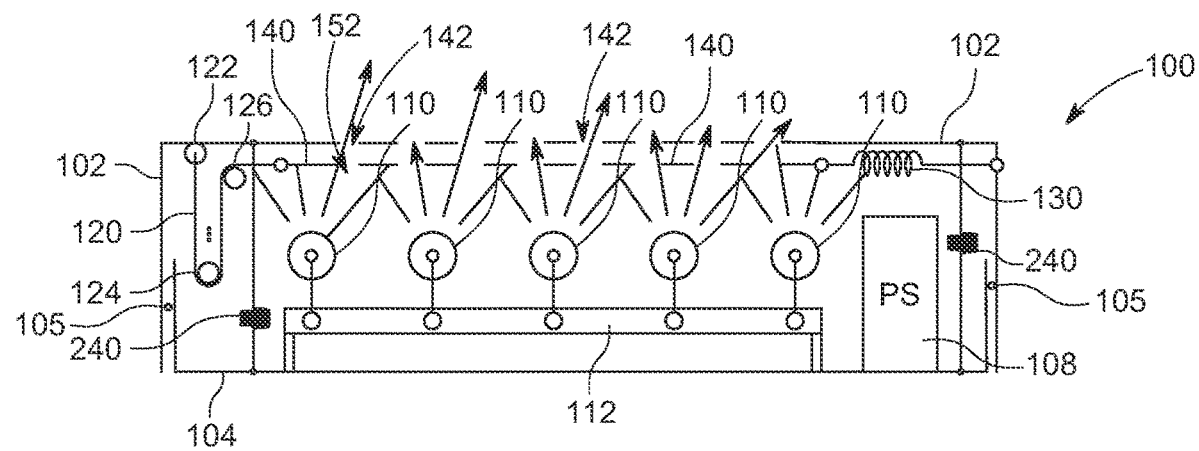
FIG. 2 illustrates a side-cutaway view of the foot sanitization device with louvers/shutters after downward pressure (weight) is placed on a top section.
Figure 3:
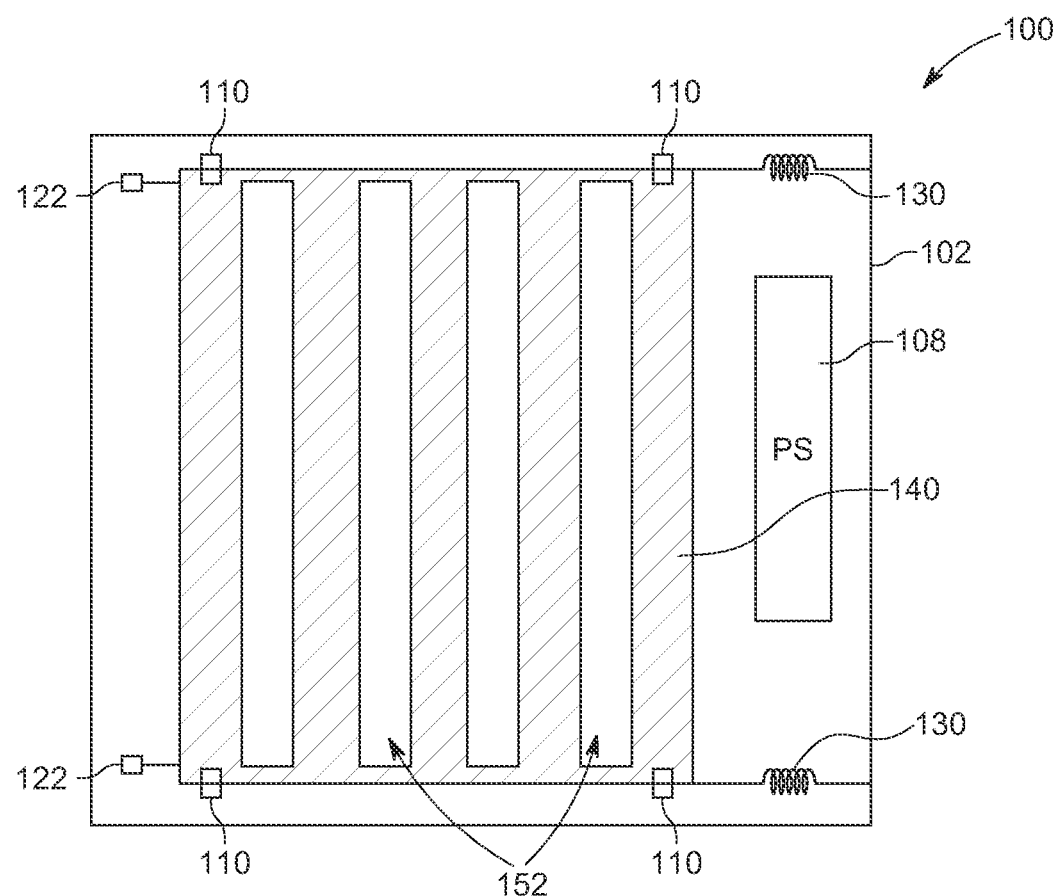
FIG. 3 illustrates a top plan view of the foot sanitization device with louvers/shutters after downward pressure (weight) is placed on a top section.

Referring to FIGS. 1, 2, and 3, views of a foot sanitization device with louvers/shutters 100 are shown before downward pressure (weight) is placed on a top section (FIG. 1) and after downward pressure (weight) is placed on a top section (FIGS. 2 and 3). In this foot sanitization device with louvers/shutters 100, the ultraviolet emitters 110 continuously emit ultraviolet light at some intensity as long as power is provided. The ultraviolet emitters 110 are typically mercury vapor tubes without any coating material that impedes the passing of ultraviolet light, including ultraviolet light in the 253.7 wavelength range which is very good at destroying pathogens. The ultraviolet emitters 110 emit a broader range of ultraviolet that includes the 254 nm wavelength (e.g., 253.7 nm) and also emit shorter wavelength ultraviolet light (e.g., approximately 180 nm) for the production of ozone in the presence of oxygen ($O_2$). The shorter wavelength ultraviolet light will break the bond between dioxygen molecules ($O_2$+UV→2O), then the unstable oxygen atoms bond with another dioxygen molecule ($O_2$+O→$O_3$) forming ozone. The ozone will help in destroying pathogens that are not easily destroyed solely with the higher wavelength of ultraviolet light.

Prior foot sanitization devices sensed when a user stood on the device, much like a bathroom scale, and energized the ultraviolet emitters 110 each time a user is sensed to prevent the emission of ultraviolet light when the feet of a user is not present. This operation requires applying power to the ultraviolet emitters 110 then removing power from the ultraviolet emitters 110 every time a person or animal steps on the foot sanitization device. One might imagine that in a busy location, the foot sanitization devices will power cycle many times in one day, sometimes for actual use for sanitization and sometimes when stepped upon due to normal passage of people/animals. As the ultraviolet emitters 110 are typically mercury vapor tubes or the like, these frequent power cycles often lead to reduced lives of the ultraviolet emitters 110 and, upon failure, the foot sanitization devices must be serviced. Such servicing is expensive as the ultraviolet emitters 110 are costly and the location of the foot sanitization devices make servicing difficult.

To increase the life of the ultraviolet emitters 110 and increase the speed of irradiation by the ultraviolet light, the foot sanitization device with louvers/shutters 100 maintains constant operation of the ultraviolet emitters 110 (either full power or reduced power) and selectively blanks, occludes, or covers openings 142 in the top-surface until a user stands on the foot sanitization device with louvers/shutters 100, thereby reducing emission of the ultraviolet light until a user stands on the foot sanitization device with louvers/shutters 100. To impact this operation, the foot sanitization device with louvers/shutters 100 has an enclosure with a top section 102 and a bottom section 104 that are movable toward and away from each other and are biased apart by compression springs 240. In most embodiments, the top section 102 and a bottom section 104 are sealed, for example with a seal 105. As the ultraviolet emitters emit the approximately 254 nm wavelength (e.g., 253.7 nm) and also the approximately 180 nm wavelength, ozone is produced in the presence of oxygen ($O_2$) within the enclosure. As the enclosure is sealed, the enclosure will not allow the escape of this ozone and ozone emission is limited to that created between the top section 102 and the user's foot/shoe for destroying pathogens.

In the closed position as shown in FIG. 1, slats of the louvers/shutters 140 cover the openings 142 in the top section 102, thereby preventing or greatly reducing emissions of ultraviolet light from the ultraviolet emitters 110 that are constantly energized/powered.

When a user stands on the top section 102, the top section 102 moves closer to the bottom section 104. As this happens, a cable 124 that is affixed to an inside surface of the top section 102 at an attach point 122 releases tension on louvers/shutters 140 that is biased in the closed position by the cable 126. As the user asserts weight/force on the top section 102, an extension spring 130 pulls the louvers/shutters 140 into the open position as shown in FIG. 2 where the openings 142 align with movable openings 152 in the louver/shutter 140, allowing the ultraviolet light to escape through slots or openings 142 in the top section 102. In this example, direction reversing pulleys 124/126 change the direction of pull of the cable 120 by 90 degrees.

For completeness, a circuit board 112 supports the ultraviolet emitters 110 and a power supply 108 is shown powering the ultraviolet emitters 110 (e.g., typically using electronic ballasts). Although not required, it is beneficial to position the ultraviolet emitters 110 directly beneath the openings 142 in the top section 102 to maximize emissions of ultraviolet light and ozone.

In FIG. 3, a partial cut-away plan view of the foot sanitization device with louvers/shutters 100. In this view, the openings 142 in the top section 102 are not aligned with movable openings 152 in the louvers/shutters 140 and, therefore, the ultraviolet emitters 110 are occluded by the louvers/shutters 140 and little or no ultraviolet light escapes through the openings 142, that is until a user places sufficient weight on the top section 102 of the foot sanitization device with louvers/shutters 100. After sufficient weight is exerted on the top section 102, the louvers/shutters 140 move into a position in which the openings 142 in the top section 102 are aligned with movable openings 152 in the louvers/shutters 140 and, therefore, ultraviolet light from the ultraviolet emitters 110 passes out of the openings 142 and radiates the user's foot/shoe with ultraviolet light, thereby generating ozone between the user's shoe/foot and the top section 102.

Note that, for brevity and clarity reasons, the views show openings 142 in the louvers/shutters 140 that are somewhat rectangular and similar openings 142 in the top section 102 of the foot sanitization device with louvers/shutters 100. There is no restriction on the size/shape of the openings nor that both be of similar size and/or shape. Further, it is desirable to seal the foot sanitization device with louvers/shutters 100 to prevent intrusion of foreign materials such as dirt and moisture and to reduce the risk of electrocution. Therefore, it is fully anticipated that the openings 142 be covered/sealed by a material that permits the passing of all desired wavelengths of ultraviolet light, including, but not limited to 253.7 nm and 180 nm. By allowing emission of both wavelengths, optimal destruction of pathogens is performed above the top section 102 of the foot sanitization device with louvers/shutters 100 by way of the 180 nm ultraviolet light creating ozone from oxygen that is between the top section 102 of the foot sanitization device with louvers/shutters 100 and the user's foot/shoe while radiating the user's foot/shoe with all emitted bands of ultraviolet light (e.g., 253.7 nm and 180 nm). For this, it has anticipated that, in some embodiments, the openings covered or sealed with a material made from fused silica or fused quartz that provides this sealing feature while allowing passage of all desired wavelengths of ultraviolet light. Note that this sealing feature is not shown to clarity reasons.

Note that although the louvers/shutters 140 is shown utilizing linear movement from a first position in which the louvers/shutters 140 blocks the openings 142 into a second position in which the louvers/shutters 140 do not block the openings 142, any type of movement is anticipated. For example, a rotary movement is anticipated in which the louver has blades that rotate from a first position in which the blades occlude blade-shaped openings in the top section 102 into a second position in which the blades don't occlude the blade-shaped openings.

Figure 4:
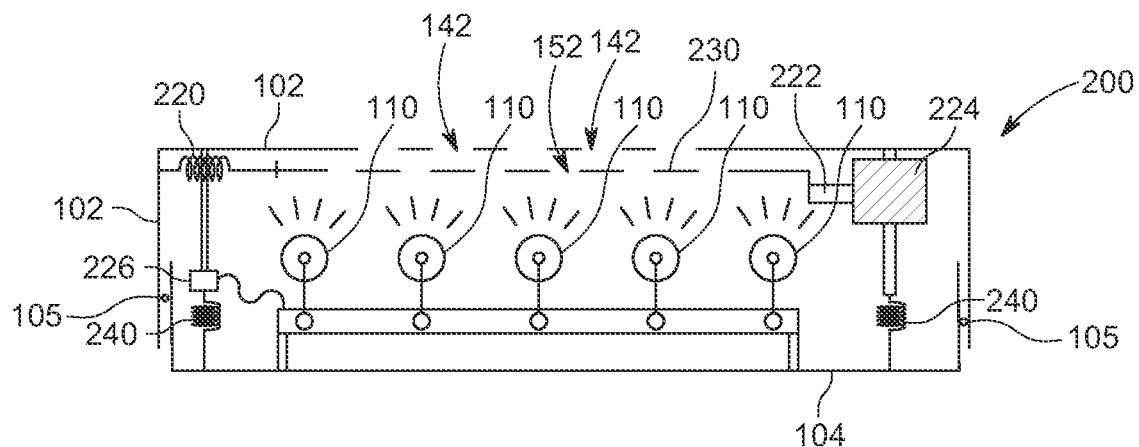
FIG. 4 illustrates a side-cutaway view of an alternate foot sanitization device with louvers/shutters before downward pressure (weight) is placed on a top section.
Figure 5:
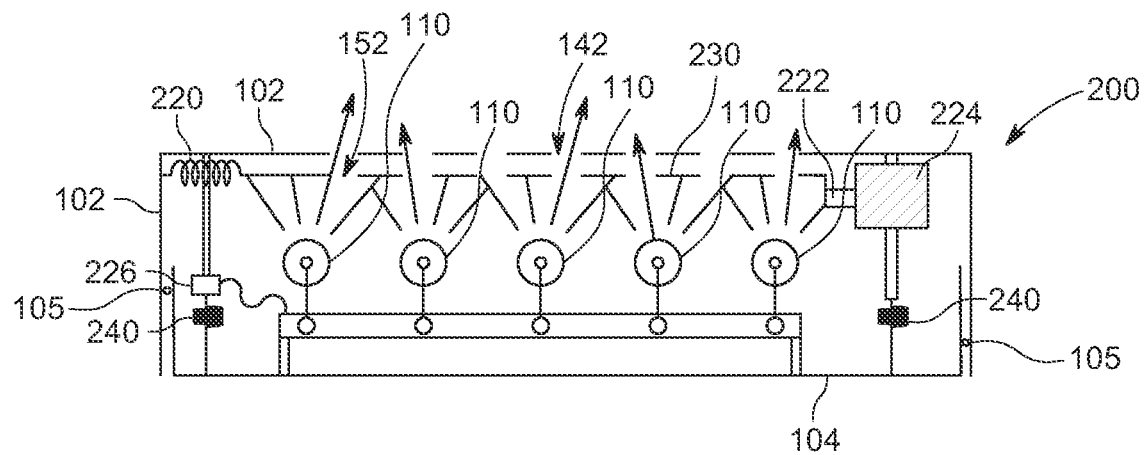
FIG. 5 illustrates a side-cutaway view of the alternate foot sanitization device with louvers/shutters after downward pressure (weight) is placed on a top section.
Figure 6:
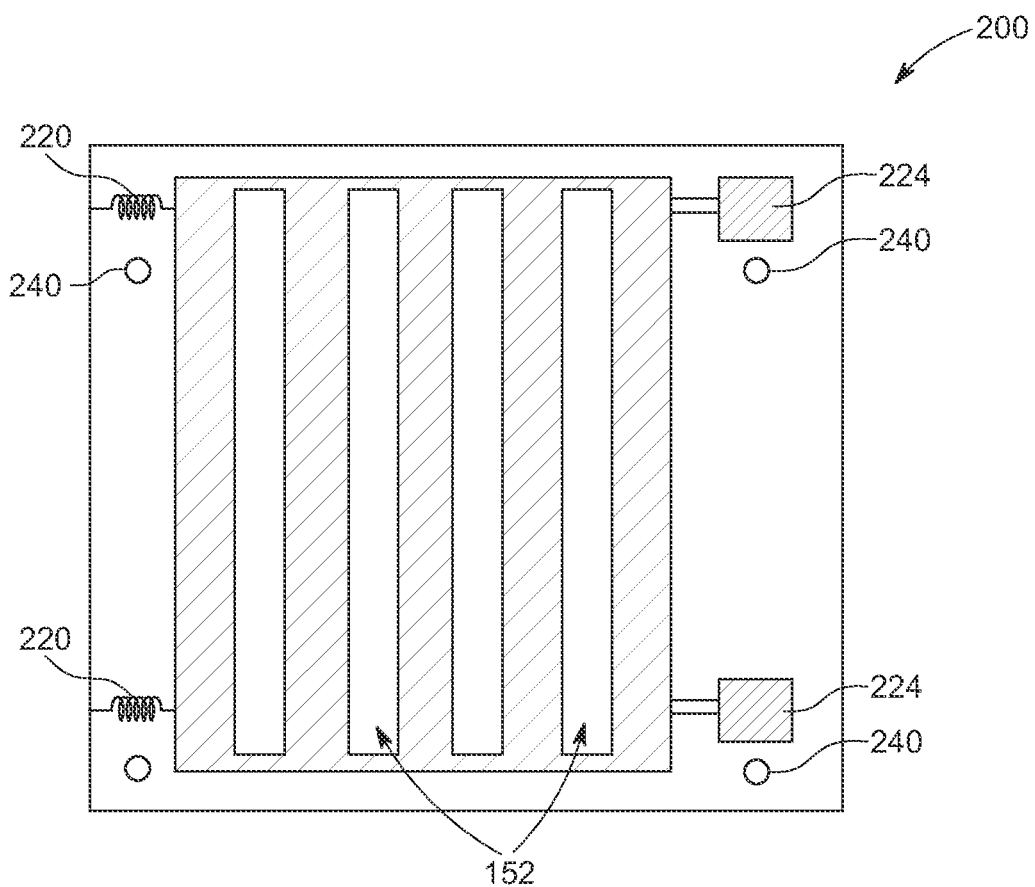
FIG. 6 illustrates a top plan view of the alternate foot sanitization device with louvers/shutters after downward pressure (weight) is placed on a top section.

Referring to FIGS. 4, 5, and 6, views of an alternate foot sanitization device with louvers/shutters 200 are shown before downward pressure (weight) is placed on a top section (FIG. 4) and after downward pressure (weight) is placed on a top section (FIG. 5). In this alternate foot sanitization device with louvers/shutters 200, the ultraviolet emitters 110 continuously emit ultraviolet light at full intensity or at a reduced intensity. The ultraviolet emitters 110 are typically mercury vapor tubes without any coating material that impedes the passing of ultraviolet light, including ultraviolet light in the 253.7 wavelength range which is very good at destroying pathogens. The ultraviolet emitters 110 emit a broader range of ultraviolet that includes the 254 nm (e.g., 253.7 nm) wavelength and also emit shorter wavelength ultraviolet light (e.g., approximately 180 nm) for the production of ozone in the presence of oxygen ($O_2$). The shorter wavelength ultraviolet light will break the bond between dioxygen molecules ($O_2 + UV \rightarrow 2O$), then the unstable oxygen atoms bond with another dioxygen molecule ($O_2 + O \rightarrow O_3$) forming ozone. The ozone will help in destroying pathogens that are not easily destroyed solely with the higher wavelength of ultraviolet light.

To increase the life of the ultraviolet emitters 110, the alternate foot sanitization device with louvers/shutters 200 maintains constant operation of the ultraviolet emitters 110 at full power or reduced power and selectively blanks, occludes, or covers openings 142 to reduce the emission of ultraviolet light from an enclosure until a user stands on the alternate foot sanitization device with louvers/shutters 200. To impact this operation, the foot sanitization device with louvers/shutters 100 has an enclosure with a top section 102 and a bottom section 104 that are movable toward and away from each other and are biased apart by compression springs 240. In most embodiments, the top section 102 and a bottom section 104 are sealed, for example with a seal 105. As the ultraviolet emitters emit the approximately 254 nm wavelength (e.g., 253.7 nm) and also the approximately 180 nm wavelength, ozone is produced in the presence of oxygen ($O_2$) within the enclosure. As the enclosure is sealed, the enclosure will not allow the escape of this ozone and ozone emission is limited to that created between the top section 102 and the user's foot/shoe for destroying pathogens.

In the closed position as shown in FIG. 4, slats of the electro-mechanically moved louver 230, align with and cover the openings 142 in the top section 102, thereby preventing or greatly reducing emissions of ultraviolet light from the ultraviolet emitters 110 that are constantly energized/powered.

When a user stands on the top section 102, the top section 102 moves closer to the bottom section 104. As this happens, a pressure sensor 226 (e.g., a pressure transducer, strain gauge) detects the increase in pressure from the weight of the user and signals the circuitry (e.g., circuitry on the circuit board 112) to energize the electro-mechanical device 224. In this example, the electro-mechanical device is a solenoid having a movable magnetic core 222. The electro-mechanical device 224 pulls the electro-mechanically moved louver 230 (in some embodiments, pushes the electro-mechanically moved louver 230) into the open position as shown in FIG. 5, allowing the ultraviolet light to escape through slots or openings 142 in the top section. In this example, an extension spring 220 biases the electro-mechanically moved louver 230 into the closed position when the electro-mechanical device 224 is not active.

In some embodiments, when the pressure sensor 226 detects a certain pressure (e.g., a pressure from a person of 80 pounds or more), the pressure sensor signals the circuitry to energize the electro-mechanical device 224. In some embodiments, the pressure sensor 226 detects a range of pressures and the pressure sensor signals the circuitry with this range and the circuitry energizes the electro-mechanical device 224 based upon a preset or configurable pressure.

In some embodiments, the ultraviolet emitters 110 are continuously powered at the same intensity as long as input power (e.g., 120 VAC) is provided. In some embodiments, power to the ultraviolet emitters 110 is varied, for example, set to 80% power when the circuitry de-energizes the electro-mechanical device 224 (e.g., no user's feet/shoes are present) and set to 100% power when the circuitry energizes the electro-mechanical device 224 (e.g., a user's fee/shoes are present).

For completeness, a circuit board 112 supports the ultraviolet emitters 110 is shown supporting the ultraviolet emitters 110 and in some cased, the electronic ballasts. The power supply 108 is left out for clarity reasons.

In FIG. 5, a partial cut-away plan view of alternate foot sanitization device with louvers/shutters 200. In this view, the openings 142 are not aligned with movable openings 152 in the electro-mechanically moved louver 230 and, therefore, the ultraviolet emitters 110 are occluded by the louvers/shutters 140 and little or no ultraviolet light escapes through the openings 142, that is until a user places sufficient weight on the top section 102 of the foot sanitization device with louvers/shutters 100 and the electro-mechanical devices 224 are energized to move the electro-mechanically moved louver 230 to the open position.

Note that, for brevity and clarity reasons, the views show the movable openings 152 in the electro-mechanically moved louver 230 that are substantially rectangular and openings 142 in the top section 102 of the alternate foot sanitization device with louvers/shutters 200 that are similar in size and shape. There is no restriction on the size/shape of the openings 142 and movable openings 152 nor that both be of similar size and/or shape. Further, it is desirable to seal the alternate foot sanitization device with louvers/shutters 200 to prevent intrusion of foreign materials such as dirt and moisture and to reduce the risk of electrocution. Therefore, it is fully anticipated that the openings 142 be covered or sealed by a material that permits the passing of all desired wavelengths of ultraviolet light, including, but not limited to 253.7 nm and 180 nm. By allowing emission of both wavelengths, optimal destruction of pathogens is performed above the top section of the alternate foot sanitization device with louvers/shutters 200 by way of the 180 nm ultraviolet light creating ozone from oxygen that is between the top section 102 of the alternate foot sanitization device with louvers/shutters 200 and the user's foot/shoe while radiating the user's foot/shoe with all emitted bands of ultraviolet light (e.g., 253.7 nm). For this, in some embodiments, the openings covered or sealed with a material made from fused silica or fused quartz that provides this sealing feature while allowing passage of all desired wavelengths of ultraviolet light. Note that this sealing feature is not shown to clarity reasons.

Figure 7:
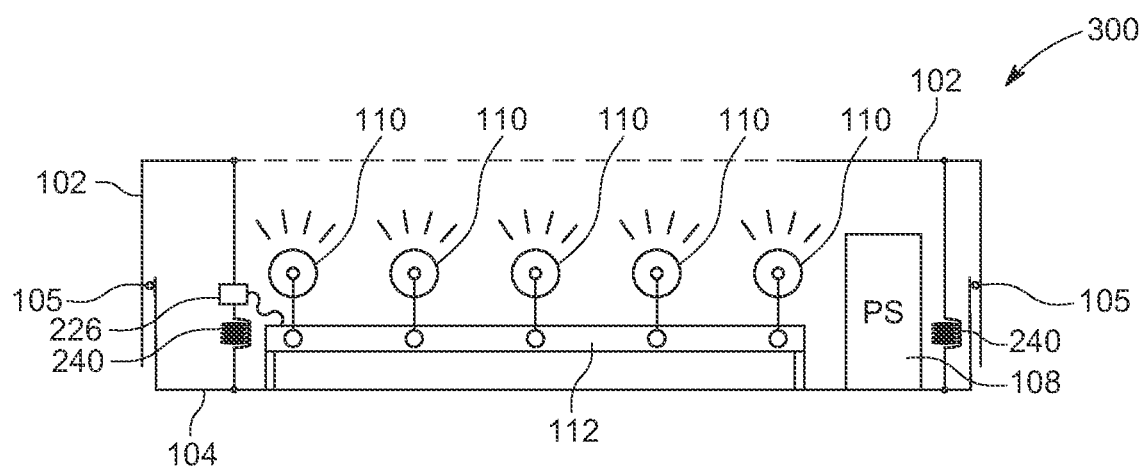
FIG. 7 illustrates a side-cutaway view of a third foot sanitization device before downward pressure (weight) is placed on a top section.

Referring to FIG. 7, a side-cutaway view of a third foot sanitization device 300 before downward pressure (weight) is placed on a top section is shown. In this embodiment, the ultraviolet emitters 110 constantly radiate ultraviolet light towards the top section 102 of the third foot sanitization device 300. In such, the top section 102 is biased away from the bottom section 104 by compression springs 240 and, again, there is a pressure sensor 226 for detecting pressure placed upon the top section 102 of the third foot sanitization device 300. In such, the ultraviolet emitters 110 are powered and emit a lower amount of ultraviolet light energy until the pressure sensor 226 detects the user stepping upon the top section 102 of the third foot sanitization device 300 (e.g., detects a predetermined force on the top section 102), at which time the pressure sensor 226 signals the internal electronic circuitry to increase the power to the ultraviolet emitters 110, thereby increasing the amount of ultraviolet light energy that is emitted towards the feet/shoes of the user (not shown for clarity and brevity reasons).

In some embodiments, the ultraviolet emitters 110 are powered with a predetermined percentage of power (e.g., 80% power) when the pressure sensor 226 detects absence of pressure or a pressure that is less than a predetermined pressure and when the pressure sensor 226 detects a certain pressure (e.g., a pressure greater than a predetermined pressure such as from a person of 80 pounds or more), the pressure sensor signals the circuitry to energize the ultraviolet emitters 110 at full power. In some embodiments, the pressure sensor 226 detects a range of pressures and the pressure sensor signals the circuitry with this range and the circuitry energizes the ultraviolet emitters 110 based upon a preset, predetermined, or configurable pressure.

In most embodiments, the top section 102 and a bottom section 104 are sealed, for example with a seal 105. As the ultraviolet emitters emit the approximately 254 nm wavelength (e.g., 253.7 nm) and also the approximately 180 nm wavelength, ozone is produced in the presence of oxygen ($O_2$) within the enclosure. As the enclosure is sealed, the enclosure will not allow the escape of this ozone and ozone emission is limited to that created between the top section 102 and the user's foot/shoe for destroying pathogens.

Figure 8:
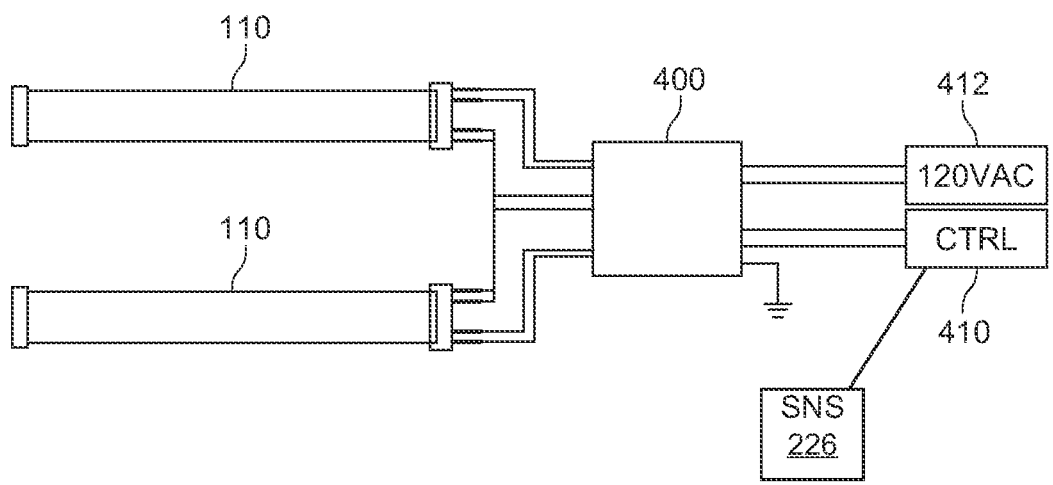
FIG. 8 illustrates a partial schematic view of the third foot sanitization device.

FIG. 8 illustrates a partial schematic view of the third foot sanitization device 300. In this, the pressure sensor 226 is connected to a control circuit 410 that controls one or more ballasts 400. The ballasts 400 receive line voltage (e.g., 120

VAC) from a power source 412. Responsive to a user standing on the third foot sanitization device 300, the pressure sensor 226 signals the control circuit 410 to modify the power (e.g., voltage, frequency, and/or duty cycle) provided by the ballasts 400 to the ultraviolet emitters 110. In such, the ultraviolet emitters 110 are always powered (when connected to a power source 412) and in absence of a requisite pressure as detected by the pressure sensor 226, power to the ultraviolet emitters 110 is set to a value less than full power and in the presence of the requisite pressure (e.g., an object such as a human stands on the top section of the enclosure), power to the ultraviolet emitters 110 is set to full power. Note that full power is a value that causes the ultraviolet emitters 110 to emit sufficient ultraviolet light to destroy pathogens and generate ozone from oxygen molecules that are above the foot sanitization device with louvers/shutters 100. In some embodiments, the power applied to the ultraviolet emitters 110 is proportional to the pressure as detected by the pressure sensor 226 but the power is not reduced to less than a minimum power level that provides for ultraviolet emitter 110 enhanced life and fast response to a user stepping on the foot sanitization device with louvers/shutters 100. As such, when a smaller human steps on the foot sanitization device with louvers/shutters 100, less power is provided to the ultraviolet emitters 110 than when a larger human steps on the foot sanitization device with louvers/shutters 100.

Note that, for brevity and clarity reasons, any combination of the above embodiments is fully anticipated, for example, opening/closing of louvers/shutters 140 and reducing power to the ultraviolet emitters 110 when the louvers/shutters 140 are closed and increasing power to the ultraviolet emitters 110 when the louvers/shutters 140 are open. Note that although the louvers/shutters 140 are shown predominately as louvers that move laterally, it is equally anticipated that the openings 142 be covered by shutters that are opened mechanically or electromechanically when the force is applied to the top section 102.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

The invention claimed is:

1. A foot/shoe sanitization device comprising:
at least one ultraviolet emitter housed within an enclosure, a top section of the enclosure having at least one opening for passing ultraviolet light from the at least one ultraviolet emitter, the at least one ultraviolet emitter continuously powered to emit the ultraviolet light;
means for selectively occluding each of the at least one opening, the means for occluding having an open position in which each of the at least one opening allowing passage of the ultraviolet light out of the enclosure and a closed position in which each of the at least one opening is occluded, thereby blocking the passage of the ultraviolet light out of the enclosure, the means for selectively occluding being biased into the closed position; and
means for detecting a force as applied to the top section of the enclosure, the means for detecting the force electrically controlling an electromechanical device, the electromechanical device interfaced between the enclosure and the means for selectively occluding, such that, the electromechanical device effecting movement of the means for selectively occluding from the closed position into the open position when the means for detecting is detecting the force at a value greater than a predetermined force, thereby, releasing the ultraviolet light out of the enclosure through the at least one opening when the predetermined force is applied to the top section.

2. The foot/shoe sanitization device of claim 1, wherein when means for detecting the force detects the force being less than the predetermined force, the means for detecting the force electrically controlling the electromechanical device, such that, the electromechanical device effecting the movement of the means for selectively occluding from the open position into the closed position.

3. The foot/shoe sanitization device of claim 1, wherein the at least one ultraviolet emitter emits light in a 254 nm wavelength and in a 180 nm wavelength.

4. The foot/shoe sanitization device of claim 1, further comprising means for sealing the at least one opening.

5. The foot/shoe sanitization device of claim 4, wherein the means for sealing the at least one opening comprises a material selected from a group consisting of fused silica and fused quartz.

6. The foot/shoe sanitization device of claim 1, wherein the means for detecting the force comprises a pressure sensor.

7. The foot/shoe sanitization device of claim 1, wherein the means for detecting the force signals an electronic circuit within the enclosure such that the electronic circuit operates the at least one ultraviolet emitter at a full power output in the open position and the electronic circuit operates the at least one ultraviolet emitter at less-than the full power output in the closed position.

8. The foot/shoe sanitization device of claim 1, further comprising a seal between the top section of the enclosure and a bottom section of the enclosure, the seal reducing ozone from escaping out of the enclosure.

9. A foot/shoe sanitization device comprising:
at least one ultraviolet emitter housed within an enclosure, a top section of the enclosure having at least one opening for passing ultraviolet light from the at least one ultraviolet emitter to an area outside of the enclosure, the at least one ultraviolet emitter continuously powered to emit the ultraviolet light, the enclosure having a bottom section;
a louver, the louver slideably interfaced to the enclosure beneath the top section, the louver having at least one louver opening, the louver is movable between an open position in which the at least one louver opening aligns with the at least one opening of the top section and a closed position in which the louver blocks each of the at least one opening of the top section, the louver biased into the closed position;
springs, the springs biasing the top section of the enclosure away from the bottom section of the enclosure;
a pressure sensor arranged between the top section of the enclosure and the bottom section of the enclosure, the pressure sensor measuring a force placed upon the top section of the enclosure; and an electromechanical device mechanically linked between the enclosure and the louver such that, upon a predetermined force detected by the pressure sensor, the electromechanical device moves the louver from the closed position towards the open position, enabling the ultraviolet light to exit through the at least one opening of the top section.

10. The foot/shoe sanitization device of claim 9, wherein the at least one ultraviolet emitter emits the ultraviolet light in a 254 nm wavelength and in a 180 nm wavelength.

11. The foot/shoe sanitization device of claim 9, further comprising means for sealing the at least one opening.

12. The foot/shoe sanitization device of claim 11, wherein the means for sealing the at least one opening comprises a material selected from a group consisting of fused silica and fused quartz.

13. The foot/shoe sanitization device of claim 9, wherein the electromechanical device is a solenoid.

14. The foot/shoe sanitization device of claim 9, further comprising a seal between the top section of the enclosure and the bottom section of the enclosure, the seal reducing ozone leakage escaping out of the enclosure.

15. A foot/shoe sanitization device comprising:

at least one ultraviolet emitter housed within an enclosure, a top section of the enclosure having at least one opening for passing ultraviolet light from the at least one ultraviolet emitter, the at least one ultraviolet emitter continuously powered to emit the ultraviolet light, the enclosure having a bottom section;

at least one shutter, the at least one shutter is rotatably interfaced to the enclosure beneath the top section, the at least one shutter is rotatable between an open position in which the ultraviolet light passes from the at least one ultraviolet emitter and out of the enclosure through the at least one opening, and into a closed position in which the at least one shutter blocks the ultraviolet light from leaving the enclosure, the at least one shutter is biased into the closed position;

springs, the springs biasing the top section of the enclosure away from the bottom section of the enclosure;

a pressure sensor arranged between the top section of the enclosure and the bottom section of the enclosure, the pressure sensor measuring a force placed upon the top section of the enclosure; and an electromechanical device mechanically linked between the enclosure and each of the at least one shutter such that, upon a predetermined force detected by the pressure sensor, the electromechanical device moves the at least one shutter from the closed position towards the open position, thereby enabling the ultraviolet light to exit through the at least one opening.

16. The foot/shoe sanitization device of claim 15, further comprising means for sealing the at least one opening.

17. The foot/shoe sanitization device of claim 16, wherein the means for sealing the at least one opening comprises a material selected from a group consisting of fused silica and fused quartz.

18. The foot/shoe sanitization device of claim 15, wherein the electromechanical device is a solenoid.

19. The foot/shoe sanitization device of claim 15, further comprising a seal between the top section of the enclosure and the bottom section, the seal reducing ozone leakage from escaping out of the enclosure.

20. The foot/shoe sanitization device of claim 15, wherein the at least one shutter is biased into the closed position by at least one biasing spring.

* * * * *